(12) United States Patent
Siddiqui et al.

(10) Patent No.: US 11,478,373 B2
(45) Date of Patent: *Oct. 25, 2022

(54) ORTHOTIC DEVICE WITH SNAP FIT CUFF AND LATCH MECHANISM

(71) Applicant: VISION QUEST INDUSTRIES INCORPORATED, Irvine, CA (US)

(72) Inventors: Masood Siddiqui, Irvine, CA (US); Michael S. Skahan, Ramona, CA (US); Kevin R. Lunau, Valley Center, CA (US)

(73) Assignee: VISION QUEST INDUSTRIES INCORPORATED, Irvine, CA (US)

( * ) Notice: Subject to any disclaimer, the term of this patent is extended or adjusted under 35 U.S.C. 154(b) by 416 days.

This patent is subject to a terminal disclaimer.

(21) Appl. No.: 16/523,743

(22) Filed: Jul. 26, 2019

(65) Prior Publication Data

US 2019/0343671 A1 Nov. 14, 2019

Related U.S. Application Data

(63) Continuation of application No. 15/097,458, filed on Apr. 13, 2016, now Pat. No. 10,369,037.

(60) Provisional application No. 62/149,029, filed on Apr. 17, 2015.

(51) Int. Cl.
*A61F 5/01* (2006.01)
*A44B 11/00* (2006.01)
*A44B 11/04* (2006.01)

(52) U.S. Cl.
CPC .......... *A61F 5/0123* (2013.01); *A44B 11/006* (2013.01); *A44B 11/008* (2013.01);
(Continued)

(58) Field of Classification Search
CPC ........ A61F 5/01; A61F 5/0102; A61F 5/0123; A44B 11/00; A44B 11/005; A44B 11/006;
(Continued)

(56) References Cited

U.S. PATENT DOCUMENTS 3,204,307 A * 9/1965 Dunn .................. A43C 11/1406
36/50.5
4,424,636 A * 1/1984 Everest .............. A43C 11/1406
24/69 SK
(Continued)

*Primary Examiner* — Keri J Nelson
(74) *Attorney, Agent, or Firm* — Lawrence N. Ginsberg

(57) ABSTRACT

An orthotic device including a frame assembly and a support structure. The frame assembly includes at least one frame having a first frame opening and a second frame opening. The support structure assembly includes at least one support structure supported by the at least one frame. The at least one support structure includes a mounting portion; a slide engagement member supported by the mounting portion configured to engage the first frame opening; and, at least one snap engagement member supported by the mounting portion configured to engage the second frame opening. The slide engagement member and the at least one snap engagement member are integrally formed with the mounting portion. In another embodiment the orthotic device includes a latch mechanism including a lever assembly, a draw bar, a chafe, a catch, and a first snap fit ledge.

14 Claims, 6 Drawing Sheets

(52) U.S. Cl.
CPC ............... *A44B 11/04* (2013.01); *A61F 5/01* (2013.01); *A61F 5/0102* (2013.01)

(58) Field of Classification Search
CPC ....... A44B 11/008; A44B 11/02; A44B 11/04; A44B 11/258; A44B 11/2584; A44B 11/2588; A43C 11/14; A43C 11/1406
See application file for complete search history.

(56) References Cited

U.S. PATENT DOCUMENTS

| | | | | |
|---|---|---|---|---|
| 4,796,337 | A | * | 1/1989 | Marxer ............... A43C 11/1413 24/71 SK |
| 5,715,582 | A | * | 2/1998 | Zorzi ................. A43C 11/1406 24/71 SK |
| 5,884,370 | A | * | 3/1999 | Bergamin ............ A43C 11/148 24/71 SK |
| 5,974,633 | A | * | 11/1999 | Sartor ................ A43C 11/1433 24/71 SK |
| 6,145,168 | A | * | 11/2000 | Baggio .............. A43C 11/1406 24/71 SK |
| 6,347,436 | B1 | * | 2/2002 | Barber ............... A43C 11/1406 24/71 SK |
| 10,369,037 | B2 | * | 8/2019 | Siddiqui ............. A44B 11/006 |
| 2007/0077832 | A1 | * | 4/2007 | Godoy ................... A63B 31/11 441/64 |
| 2010/0174221 | A1 | * | 7/2010 | Ingimundarson ..... A61F 5/0123 602/26 |

* cited by examiner

ORTHOTIC DEVICE WITH SNAP FIT CUFF AND LATCH MECHANISM

CROSS REFERENCE TO RELATED APPLICATIONS

This application claims the benefits of U.S. application Ser. No. 15/097,458, filed Aug. 6, 2019, entitled ORTHOTIC DEVICE WITH SNAP FIT CUFF AND LATCH MECHANISM, which claims the benefit of U.S. Provisional Application Ser. No. 62/149,029, filed on Apr. 17, 2015, entitled ORTHOTIC DEVICE WITH SNAP FIT CUFF AND LATCH MECHANISM. The entire contents of Ser. No. 15/097,458 and 62/149,029 are hereby incorporated herein by reference thereto.

BACKGROUND OF THE INVENTION

1. Field of the Invention

The present invention relates generally to the field of orthopedic supports and braces, and specifically ease of use and inventive improvements to manufacturability.

2. Description of the Related Art

Orthopedic braces and supports are medical devices, and are mainly designed to be functional in nature. Over and above functionality, braces and supports are in a special category since they are worn on the body and their success is heavily dependent on easy and intuitive patient interaction. The issue of patient compliance is high on an inventor's list of design criteria since the brace does no good if the patient chooses not to wear it. Many factors contribute to a patient's choice whether to continue wearing a brace or support. Fit, functionality, and comfort are top priorities, but there is also ease of use and other human factors that have the potential to either decide success, or doom a brace/support to the patient's closet.

In addition to these considerations, there is the desire to improve manufacturability of the product, which will limit defects, improve quality, and therefore also improve the patient's experience.

Prior art includes many methods to secure the brace/support to the anatomy. The most commonly practiced method uses hook & loop straps which are ubiquitous, but do have their issues. For example, the elderly or less dexterous have complaints regarding peeling the straps apart to exit ("doff") the brace, and further complaints about the straps sticking to each other, clothing, furniture, etc. Elderly or less dexterous patients also sometimes have a difficult time exerting enough force to pull the straps tight and fasten them when entering ("donning") the brace/support. Some of the prior art includes different forms of mechanical advantage to help don the brace, coupled with means to doff the brace without peeling the straps each time.

There has been a partial response to this problem in current art, as seen in U.S. Pat. No. 8,257,293, issued to Ingimundarson et al. entitled KNEE BRACE AND METHOD FOR SECURING THE SAME. The '293 patent discloses a buckle assembly that can also be described as a draw latch mechanism.

SUMMARY OF THE INVENTION

In a broad aspect, the present invention is a latch mechanism including a lever assembly, a draw bar, a chafe, a catch, and a first snap fit latch. The lever assembly includes a lever; a lever axle depending from the lever at a first end thereof, for securing the lever to a support structure of the orthotic device; and a first snap fit hook projecting from the lever. The drawbar is pivotably attached to the lever. The chafe is attached to the drawbar. The catch extends from the support structure to receive the lever axle. The first snap fit ledge depends from the support structure to engage and hold the first snap fit hook. The catch is configured to stand substantially above a nominal height of the support structure such that the lever axle is easily received by the catch for fastening by the user.

In another broad aspect the invention is embodied as an orthotic device including a frame assembly and a support structure. The frame assembly includes at least one frame having a first frame opening and a second frame opening. The support structure assembly includes at least one support structure supported by the at least one frame. The at least one support structure includes a mounting portion; a slight engagement member supported by the mounting portion configured to engage the first frame opening; and, at least one snap engagement member supported by the mounting portion configured to engage the second frame opening. The said slide engagement member and the at least one snap engagement member are integrally formed with the mounting portion.

In one preferred embodiment, the orthotic device is shown as a knee brace with at least one latch mechanism attached to a pivotable D-ring chafe. The chafe has a slot that the strap is looped through.

The latch mechanism preferably includes a draw latch. The latch mechanism tightens and secures the straps around the user's anatomy, and also gives the user a mechanical advantage over just manually pulling the strap tight. It also allows for doffing/donning the brace without peeling the hook/loop on the straps. The latch mechanism un-clips and allows the strap to be loosened enough to remove the end of the strap, then remove the brace.

When the brace is ready to be donned again, the original strap length settings are saved, so it is very quick, easy, and convenient for the user to don the brace as compared to just a hook and loop strap alone.

The invention disclosed in U.S. Pat. No. 8,257,293 is a draw latch assembly, but it lacks ease of use when fastening it to the brace. The latch disclosed in that '293 patent includes a mushroom-shaped head that slides into a "keyhole" on the brace frame. The problem with such a design is that the user must push the head against the anatomy and softgood pad liner to get it engaged in the keyhole.

On the other hand, the present invention solves this issue by including a catch protruding from a nominal height of the main surface of the brace. The latch lever has an axle that easily slides under the catch, allowing for quick, easy, and convenient use by less dextrous or elderly patients. These types of patients are the main demographic for braces such as this, and user friendly features will aid in patient compliance and therefore positive outcomes in treatment.

Bulk or high-profile design is not an issue with this embodiment, since the catch is preferably made no taller than the main latch mechanism itself.

This embodiment includes snap-fits which are released by simply pulling up on the lever component, however there are many other ways to accomplish the fastening and release. Side push-buttons, top push-buttons are alternate embodiments. These, in turn, can be designed to have a single-push or a double-push configuration. The double side push for example, would require a "pinch" force from the user, so it would not be ideal for the elderly or patients with less hand strength. Still other means can include pivoting or rotating actions to release. Each of the above can be augmented with an additional spring-loaded feature to allow release of the mechanism.

In another broad aspect, the draw latch preferably has a pivotable chafe attached at one end where the strap is looped through a slot on the chafe. Prior art shows the entire latch mechanism pivoting. The present invention simply pivots the chafe itself at the end of the mechanism. This novel approach reduces the number of moving parts (or at least parts moving in multiple directions) and places the pivoting motion where it is most functional—at the edge of the frame where the strap meets the anatomy.

In another embodiment, the orthotic device includes fastening features built in or integrated directly into the frame components. Contrast this to prior art which requires the use of separate fastening components such as rivets or screws. This allows for quick, easy manufacturing of the product at a lower cost due to fasteners not being needed. It also results in a sleeker, better-looking product that will increase patient compliance.

The present embodiment includes a slide engagement member on the cuff that is passed through and slid across a first opening on the frame. Then a snap engagement member on the cuff is snapped through a second opening on the frame to complete the assembly. Compare this to purchasing separate rivet or screw components, then positioning the cuff and frame together, passing at least 2 rivets or screws through holes in the cuff and frame, placing the entire assembly in a pneumatic riveting machine, and finally fastening the rivets.

Rather than a "slide-&-snap," many other means for fastening the brace together can be imagined, such as a keyhole coupled with a snap fit. Another means could be a double keyhole that includes two "mushroom head" protrusions that pass through 2 keyhole openings in the frame. The keyholes are comprised of one large and one small diameter hole that allow the protrusions to pass through freely, then lock down as the cuff is slid through and snapped into the smaller of the two holes in the keyhole feature. Of course, all the embodiment features above can be interchanged between cuff and frame.

Other objects, advantages, and novel features will become apparent from the following detailed description of the invention when considered in conjunction with the accompanying drawings.

DETAILED DESCRIPTION OF THE INVENTION

Figure 1:
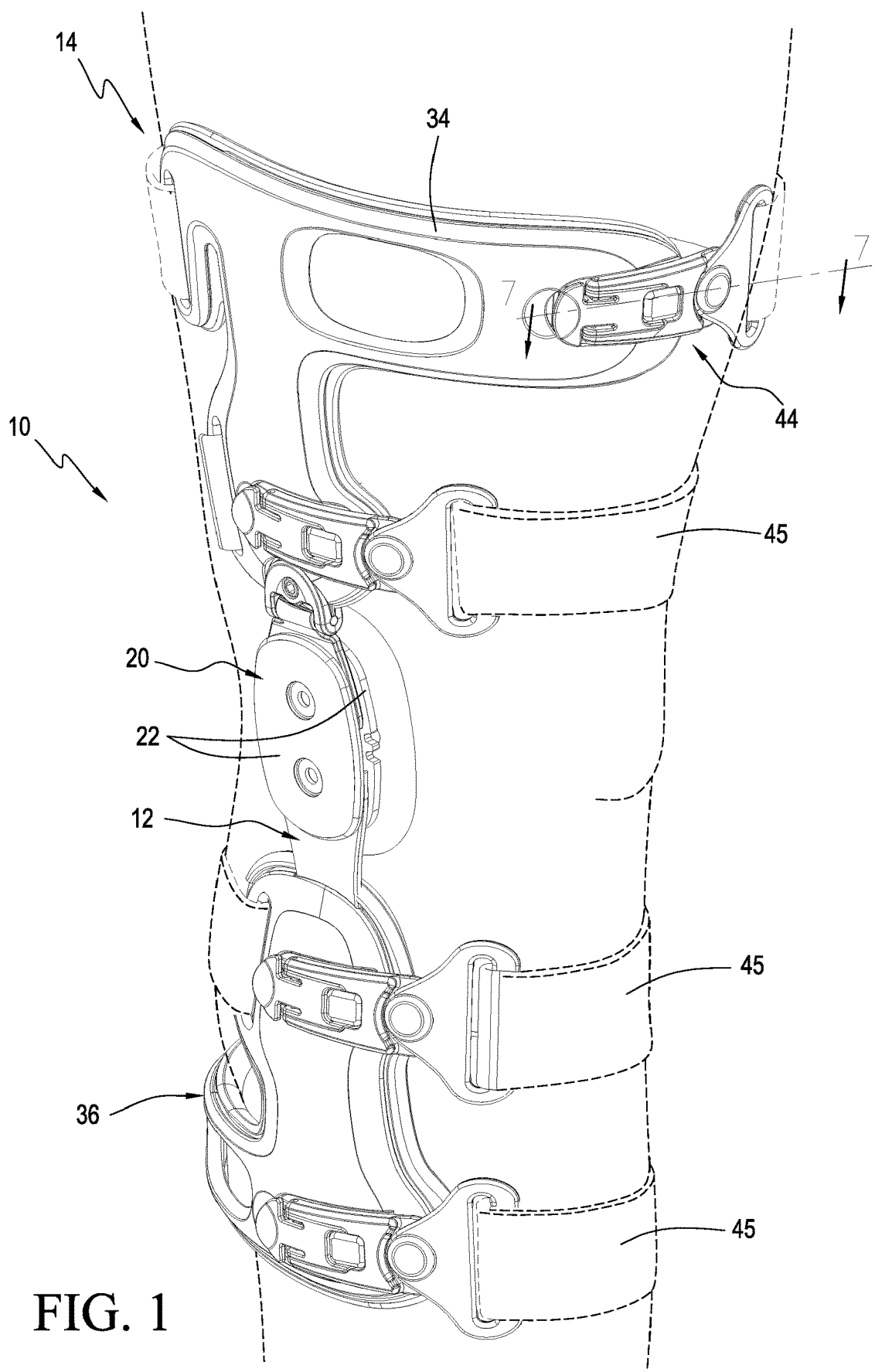
FIG. 1 is a top perspective view of the orthotic device of the present invention.
Figure 2:
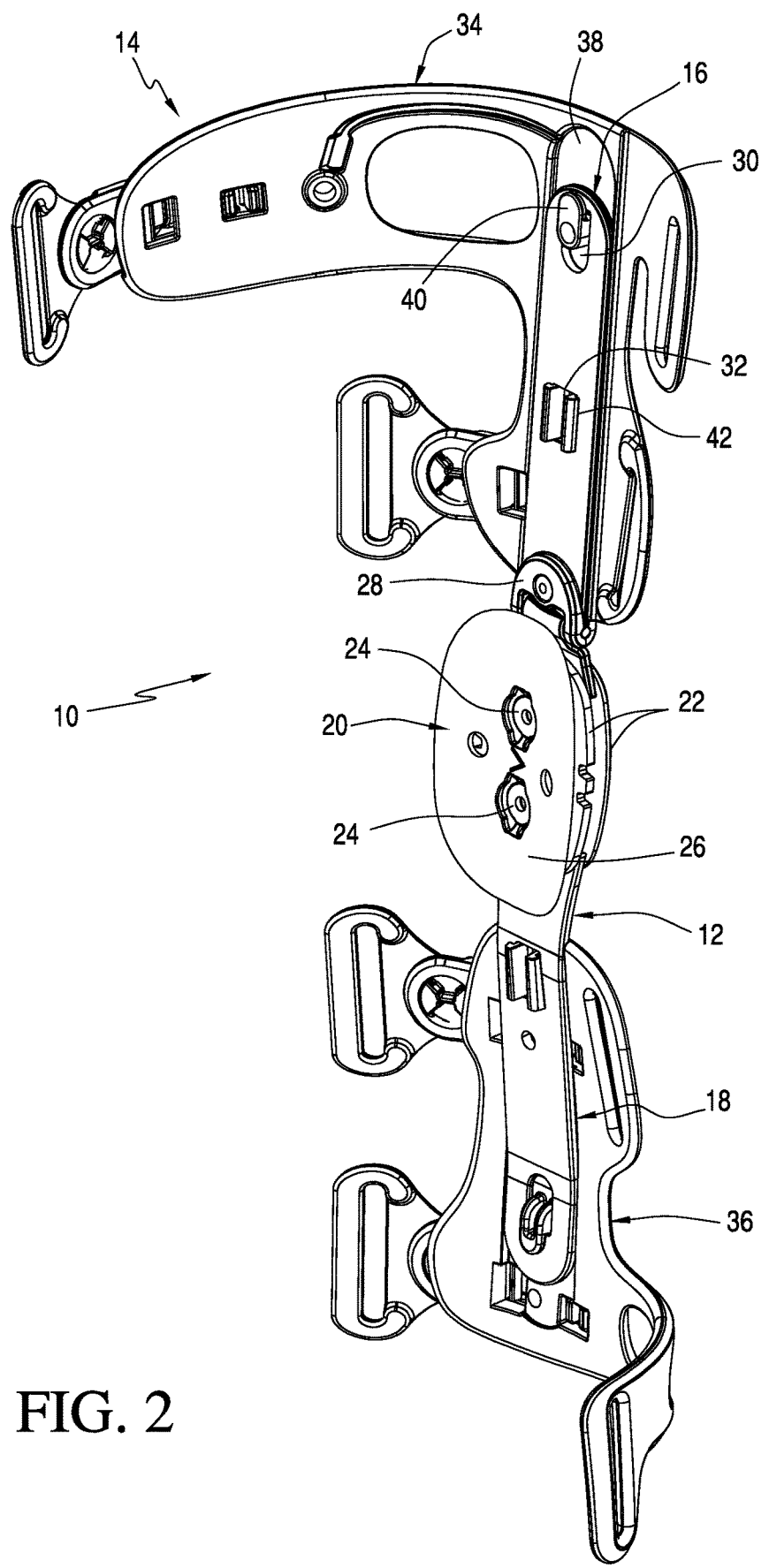
FIG. 2 is a bottom perspective view of the orthotic device.
Figure 3:
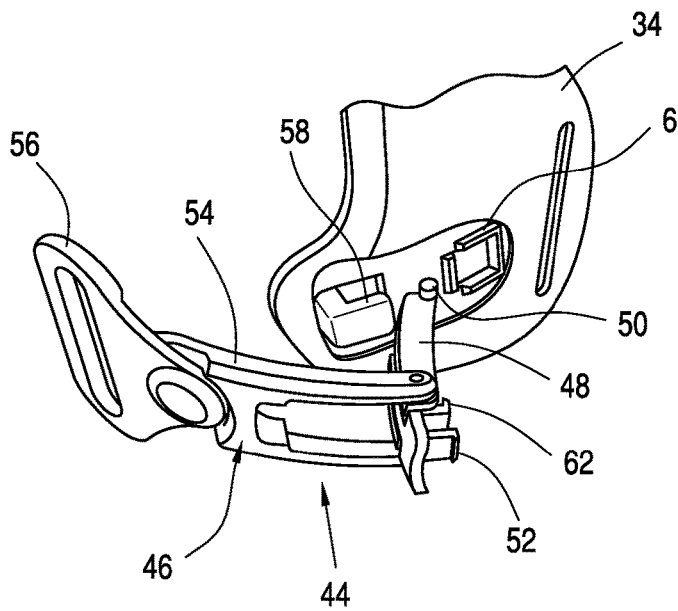
FIG. 3 is a perspective view of the orthotic device, with the latch mechanism open.
Figure 4:
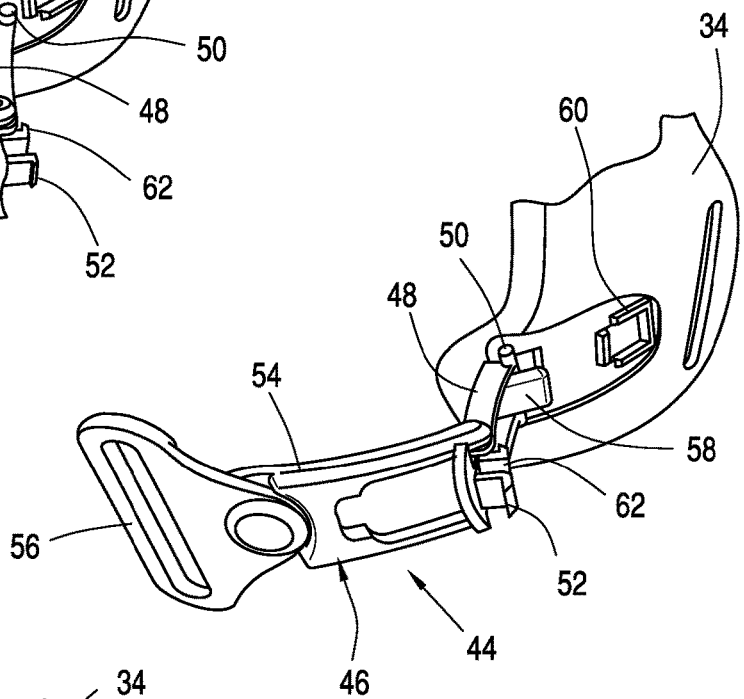
FIG. 4 is a perspective view of the orthotic device, with the lever axle attaching to the catch.
Figure 5:
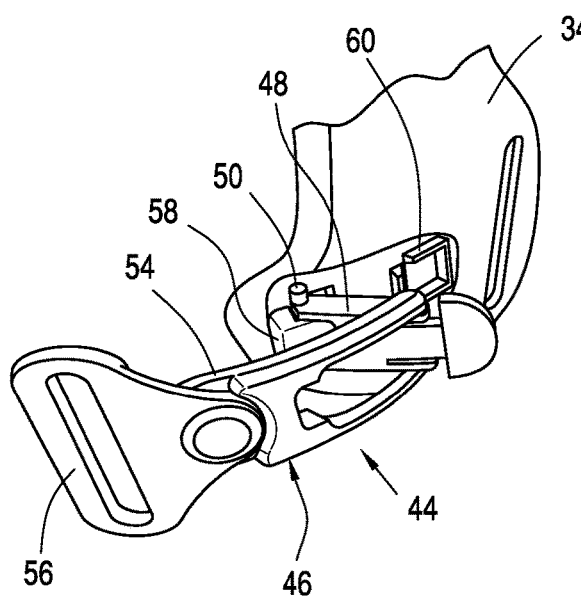
FIG. 5 is a perspective view of the orthotic device, with the lever shown moving toward closure.
Figure 6:
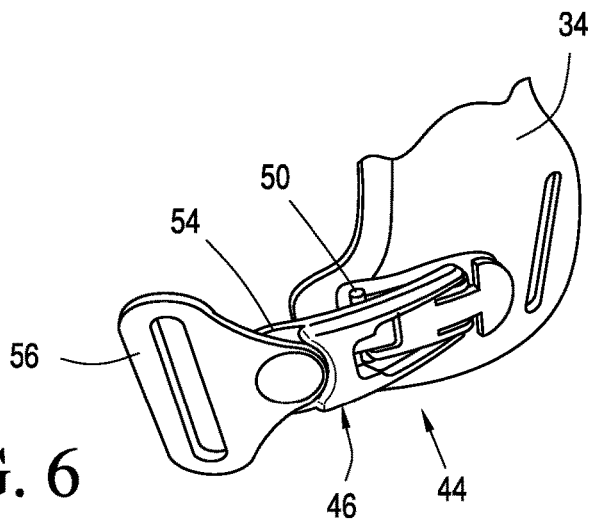
FIG. 6 is a perspective view of the orthotic device, with the latch mechanism shown closed.

Referring now to the drawings and the characters of reference marked thereon, FIGS. 1 and 2 illustrate a preferred embodiment of the present invention, designated generally as 10. The orthotic device 10 includes a frame assembly, designated generally as 12; and, a support structure assembly, designated generally as 14.

In this preferred embodiment the frame assembly 12 includes an upper frame 16 and a lower frame 18. The upper frame 16 and the lower frame 18 are connected by a hinge center assembly 20. The hinge center assembly includes hinge center plates 22, fasteners 24, and a condyle cup 26. It also includes an angulation hinge 28 for providing correction to the knee. The angulation hinge can be adjusted to angle the brace to fit the anatomy more closely. The angulation hinge can also be adjusted to allow the brace to provide an unloading force to the knee joint to help relieve knee pain. The upper frame 18 has a first frame opening 30 and a second frame opening 32.

The lower frame 18 is constructed in a similar manner as the upper frame. The upper frame and lower frame are preferably formed of metal. Alternatively, they can be formed of resilient plastic.

The support structure assembly 14 is supported by the frame assembly 12. The support structure assembly 14 includes an upper support structure 34 and a lower support structure 36. These support structures are also known in this field as "cuffs." The upper support structure 34 includes a mounting portion 38, a slide engagement member 40 supported by the mounting portion 38 and configured to engage the first frame opening 30, and at least one snap engagement member 42 supported by the mounting portion 38 and configured to engage the second frame opening 32. The slide engagement member 40 and the snap engagement member 42 are integrally formed with the mounting portion 38.

The upper support structure 34 and the lower support structure 36 are preferably formed of resilient plastic.

The present invention improves the manufacturability of the support structures and the frame assembly of the orthotic device. The most commonly heretofore practiced method to assemble the product together is the use of separate fastener parts, such as rivets or screws. The present invention eliminates these extra parts in favor of designing the fastening features directly into the parts being joined. This integration of components improves manufacturability, lowers cost, and results in a better looking product with no fasteners showing on the outside for the user to see, making the product more desirable to wear, thus increasing patient compliance.

The orthotic device 10 includes latch mechanisms, designated generally as 44, for securing straps 45 to respective support structures. Referring to FIGS. 3-6, a latch mechanism 44 is illustrated in operation. Each latch mechanism 44 includes a lever assembly, designated generally as 46. Each lever assembly 46 includes a lever 48, a lever axle 50 depending from the lever 48 at a first end thereof, for securing the lever 48 to a support structure (e.g. upper support structure 34) of the orthotic device 10; and, a first snap fit hook 52 projecting from the lever 48.

A draw bar 54 is pivotably attached to the lever 48. A chafe 56 is attached to the draw bar 54. A catch 58 extends from the support structure 34 to receive the lever axle 50. A first snap fit ledge 60 depends from the support structure 34 to engage and hold the first snap fit hook 52. The catch 58 is configured to stand substantially above a nominal height of the support structure 34 such that the lever axle 50 is easily received by the catch 58 for fastening by the user. The nominal height is the height of the outside surface of support structure 34 at the region where the catch 58 extends from the support structure 34. Thus, the term "substantially above" refers to a height above the diameter/thickness of the lever axle 50.

The chafe 56 is preferably a D-ring chafe. The lever assembly 46 preferably includes a second snap fit hook 62 spaced from the first snap fit hook 52 projecting from the lever 48.

The straps 45 may be of a conventional type typically used for braces, typically formed of woven nylon.

Figure 7:
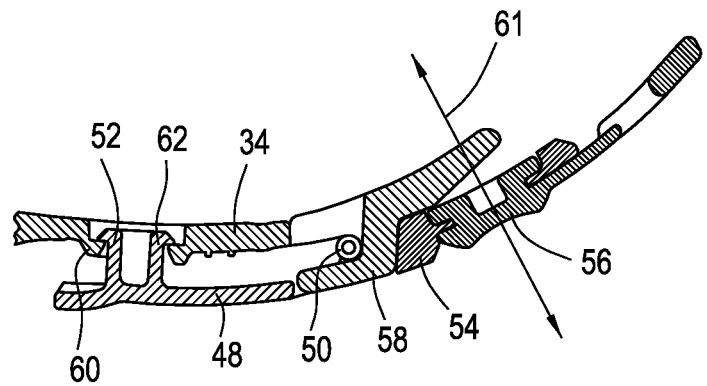
FIG. 7 is a view showing along line 7-7 of FIG. 1.

Referring now to FIG. 7, the association of the first snap fit hook 52, the second snap fit hook 62, and the upper support 34 are shown clearly when the latch mechanism is in a closed position. This figure also shows the relationship of the lever axle 50 and the catch 58. It also shows the engagement of the draw bar 54 and the chafe 56.

Figure 8:
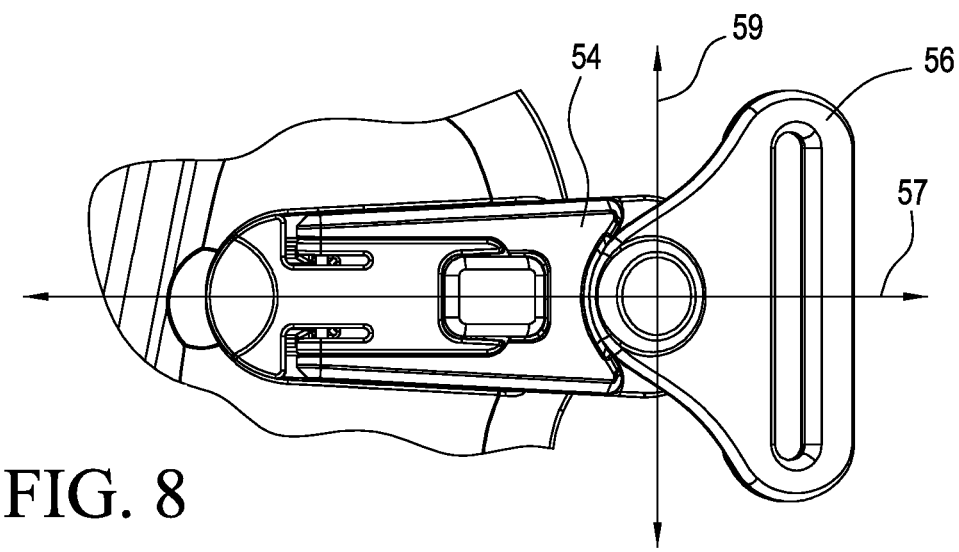
FIG. 8 is an enlarged plan view of the latch mechanism.
Figure 9:
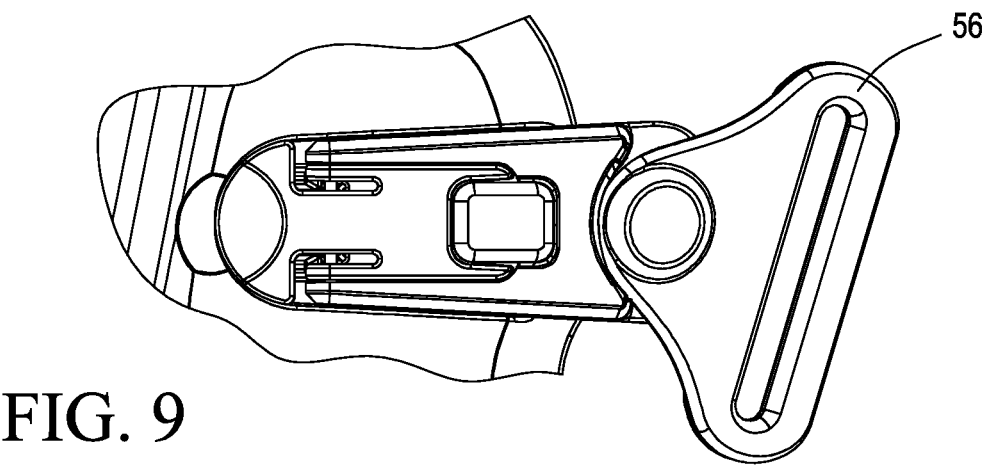
FIG. 9 shows the chafe pivoted to a different position.

FIGS. 8-9 show the pivoting motion of the chafe 56. The draw bar 54 includes a major axis 57 along the length thereof and a minor axis 59 along a width thereof. The D-ring chafe 56 is pivotably attached to the draw bar 54 around a pivot axis 61 (shown in FIG. 7) substantially perpendicular to the major axis 57 and the minor axis 59.

Figure 10:
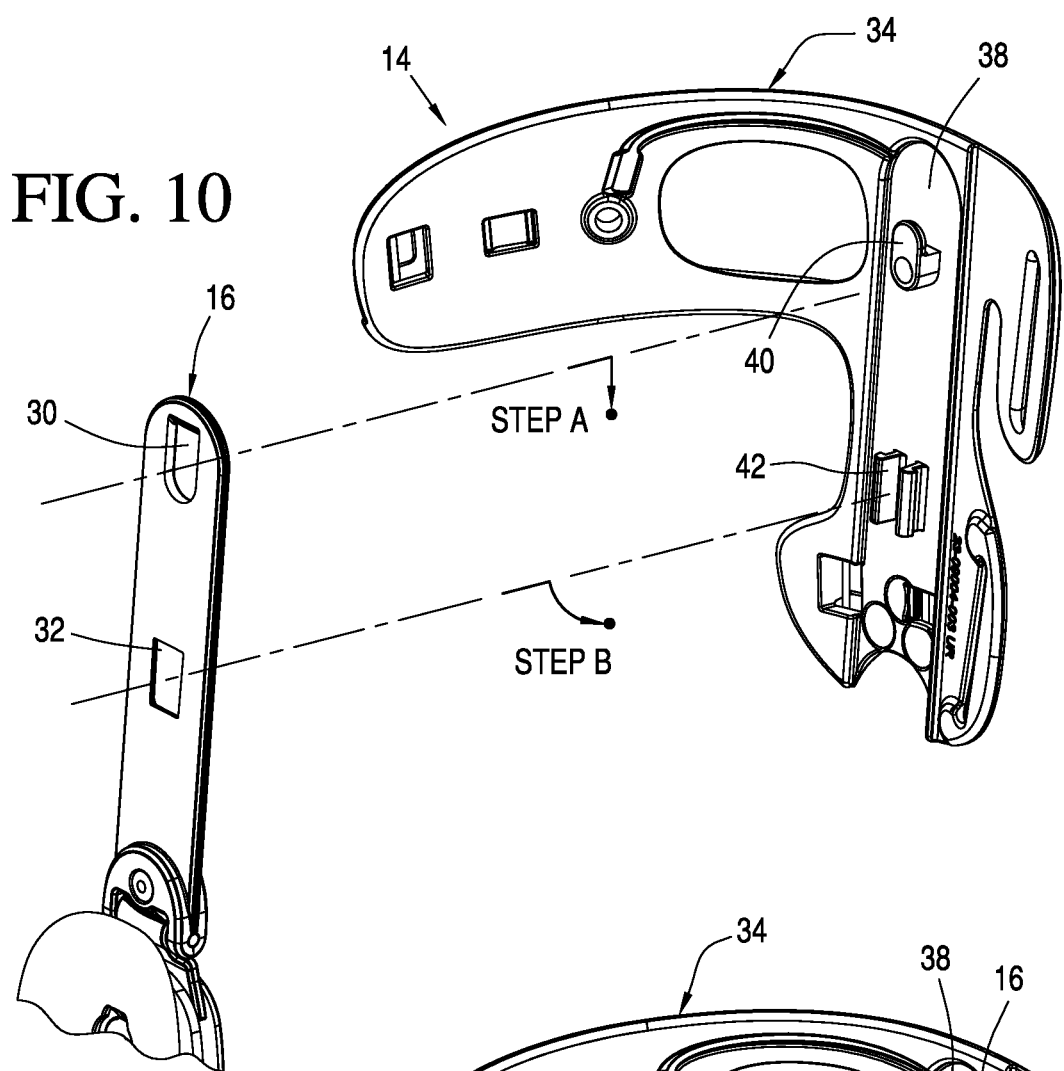
FIG. 10 is an exploded perspective view of the frame and the support structure.
Figure 11:
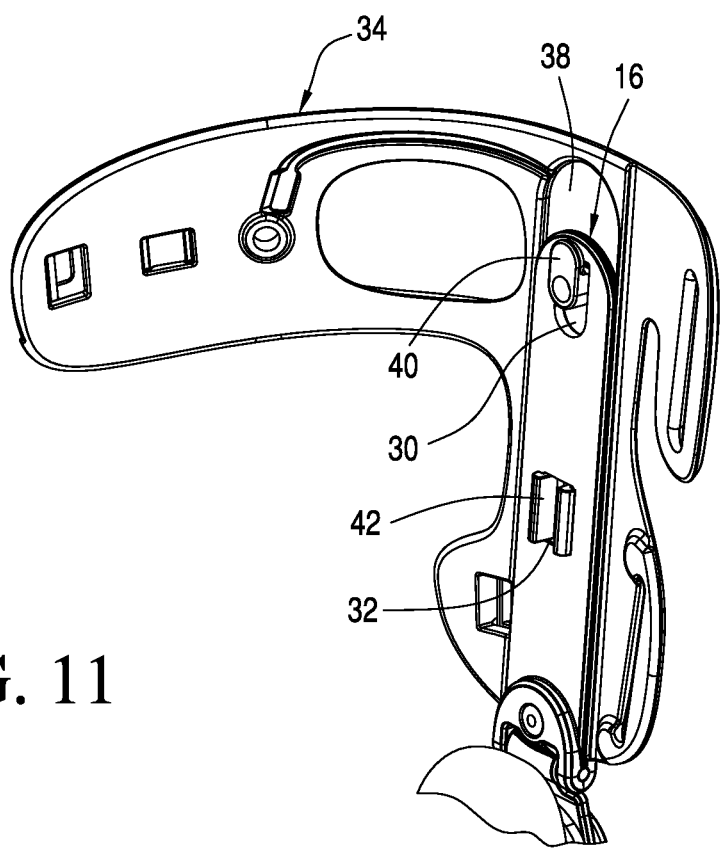
FIG. 11 is a perspective view of the frame attached to the support structure.

Referring now to FIGS. 10-11 show the first frame opening 30 engaging the slide engagement member 40 and the second frame opening 32 engaging the snap engagement member 42. The first frame opening 30 is slid over the slide engagement member 40 (as shown by Step A) then the second frame opening 32 is rotated down to snap over the snap engagement member 42 (as shown by Step B). This secures the upper frame 16 to the upper support structure 34. This obviates the use of external or separate fastening parts.

Figure 12:
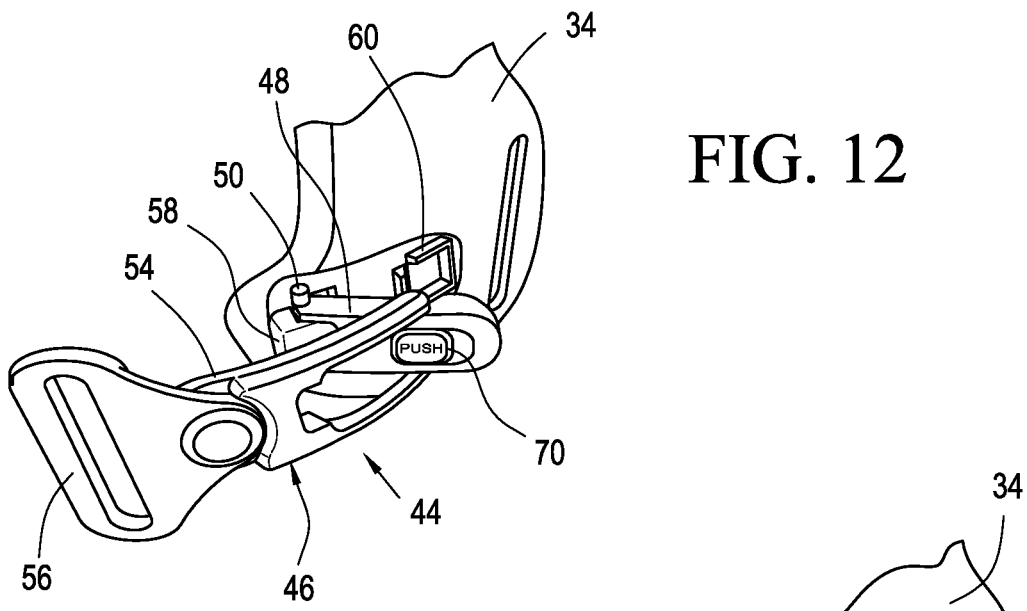
FIG. 12 is a perspective view of a portion of the orthotic device with an alternative lever utilizing a top push button.

Referring now to FIG. 12, an alternate embodiment to lever 48 is shown. This embodiment utilizes a top push button 70. Pushing the top push button 70 causes snap fit hook 52 to engage or disengage from snap fit ledge 60.

Figure 13:
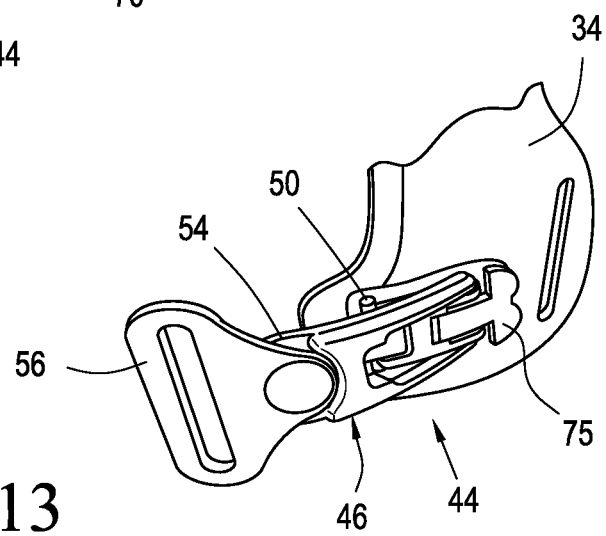
FIG. 13 is a perspective view of a portion of the orthotic device with an alternative lever utilizing a single side push button.

Similarly in FIG. 13, another alternate embodiment to lever 48 is shown. This embodiment comprises a single side push button 75. Pushing the side button 75 causes snap fit hook 52 to engage or disengage from snap fit ledge 60.

Figure 14:
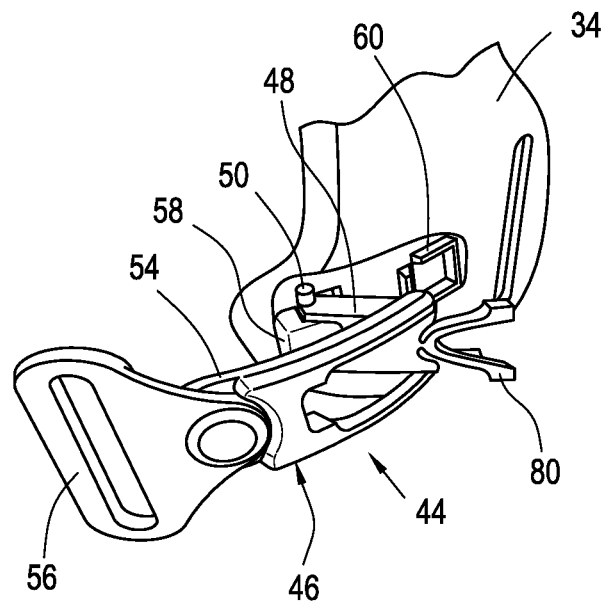
FIG. 14 is a perspective view of a portion of the orthotic device with an alternative lever utilizing a double-push configuration.

Similarly in FIG. 14, another alternate embodiment to lever 48 is shown. This embodiment comprises a double-push or "pinch" configuration 80. Pinching the double side buttons 80 causes snap fit hook 52 to engage or disengage from snap fit ledge 60.

These and other alternate embodiments to lever 48 allow greater ease of use and security by separating the direction of initiating the release from the release motion itself. For example, in FIG. 13, the direction of initiating the release when pushing button 75 is parallel to lever 48, while the release motion itself is a rotation of lever 48. Separating these two motions ultimately allows a strong and robust release force that can be started by a relatively small initiating force.

Although the invention has been described with respect to a specific embodiment it is understood that is within the scope of the invention that, for example, the orthotic device may include only an upper frame or a lower frame. Also, for example, although the support structure assembly has been described as having an upper support structure and a lower support structure, it is understood that it is within the purview of this invention to have a support structure assembly which includes only an upper support structure or a lower support structure. Although the invention has been described reference to a first and a second snap fit hook, it is understood that in some embodiments only a single snap fit hook may be used. Furthermore, additional snap fit hooks may be used. Although the rate has been shown on the lateral side of the leg it is understood that it can alternately be applied on the medial side. The inventive concepts described herein have been discussed relative to the application on a knee; however, it is within the purview of this invention to have an orthotic device that can be used on other portions of the anatomy. These other portions of the anatomy may include, for example, hands, wrists, shoulders, arms, ankles, hips, legs and spines.

Other embodiments and configurations may be devised without departing from the spirit of the invention and the scope of the appended claims.

The invention claimed is:
1. An orthotic device, comprising:
 a latch mechanism, said latch mechanism, including:
  a) a lever assembly, comprising:
   i. a lever;
   ii. a lever axle depending from said lever at a first end thereof, for securing the lever to a support structure of the orthotic device; and,
   iii. a first snap fit hook projecting from said lever;
  b) a draw bar pivotably attached to said lever;
  c) a chafe pivotably attached to said draw bar;
  d) a catch extending from the support structure to receive said lever axle; and,
  e) a first snap fit ledge depending from the support structure to engage and hold said first snap fit hook;
  wherein said chafe comprises a D-ring chafe and,
  wherein said lever axle is received by said catch for fastening by the user, and,
  wherein said chafe remains pivotable once closed.

2. The orthotic device of claim 1, wherein said lever assembly further comprises a second snap fit hook spaced from said first snap fit hook projecting from said lever.

3. The orthotic device of claim 1, further including a strap attachable to said chafe.

4. The orthotic device of claim 1, wherein said lever and said first snap fit hook are integral.

5. The orthotic device of claim 1, wherein said first snap fit hook is engaged or released from said first snap fit ledge by pulling up on said lever.

6. The orthotic device of claim 1, wherein said lever further comprises a push button that functions to engage or release said first snap fit hook from said first snap fit ledge.

7. The orthotic device of claim 1, wherein said lever further comprises a pinch configuration that functions to engage or release said first snap fit hook from said first snap fit ledge.

8. The orthotic device of claim 1, wherein said catch is configured to stand substantially above a nominal height of the support structure such that the lever axle is easily received by said catch for fastening by the user.

9. An orthotic device, comprising:
  a) a frame assembly comprising at least one frame having a first frame opening and a second frame opening;
  b) a support structure assembly comprising at least one support structure supported by the at least one frame, said at least one support structure including:
    i. a mounting portion;
    ii. a slide engagement member supported by said mounting portion configured to engage said first frame opening; and,
    iii. at least one snap engagement member supported by said mounting portion configured to engage said second frame opening,
  wherein said slide engagement member and said at least one snap engagement member are integrally formed with said mounting portion; and,
  c) a latch mechanism for securing a strap to the support structure, comprising:
    i. a lever assembly, comprising:
      a. a lever;
      b. a lever axle depending from said lever at the first end thereof, for securing the lever to the support structure of the orthotic device; and,
      c. a first snap fit hook projecting from said lever;
    ii. a draw bar pivotably attached to said lever;
    iii. a chafe pivotably attached to said draw bar;
    iv. a catch extending from the support structure to receive said lever axle; and,
    v. a first snap fit ledge depending from the support structure to engage and hold said first snap fit hook;
  wherein said chafe comprises a D-ring chafe and,
  wherein said lever axle is received by said catch for fastening by the user, and,
  wherein said chafe remains pivotable once closed.

10. The orthotic device of claim 9, wherein said lever assembly comprises a second snap fit hook spaced from said first snap fit hook projecting from said lever.

11. The orthotic device of claim 9, wherein said lever and said snap fit hook are integral.

12. The orthotic device of claim 9, wherein said snap fit hook is engaged or released from said snap fit ledge by pulling up on said lever.

13. The orthotic device of claim 9, wherein said lever comprises a push button that functions to engage or release said snap fit hook from said snap fit ledge.

14. The orthotic device of claim 9, wherein said lever comprises a pinch configuration that functions to engage or release said snap fit hook from said snap fit ledge.

* * * * *